(12) United States Patent
Buckley et al.

(10) Patent No.: US 10,088,425 B2
(45) Date of Patent: Oct. 2, 2018

(54) RAPID MATERIAL ANALYSIS USING LIBS SPECTROSCOPY

(71) Applicant: TSI, INCORPORATED, St. Paul, MN (US)

(72) Inventors: Steven G. Buckley, Redmond, WA (US); Darrick L. Niccum, Vadnais Heights, MN (US)

(73) Assignee: TSI, Incorporated, Shoreview, MN (US)

( * ) Notice: Subject to any disclaimer, the term of this patent is extended or adjusted under 35 U.S.C. 154(b) by 0 days.

(21) Appl. No.: 15/321,143

(22) PCT Filed: Jun. 19, 2015

(86) PCT No.: PCT/US2015/036617
§ 371 (c)(1),
(2) Date: Dec. 21, 2016

(87) PCT Pub. No.: WO2015/200111
PCT Pub. Date: Dec. 30, 2015

(65) Prior Publication Data
US 2017/0205354 A1    Jul. 20, 2017

(51) Int. Cl.
*B07C 5/00* (2006.01)
*G01N 21/71* (2006.01)
(Continued)

(52) U.S. Cl.
CPC ......... *G01N 21/718* (2013.01); *B07C 5/3425* (2013.01); *B07C 5/365* (2013.01);
(Continued)

(58) Field of Classification Search
CPC ...... B07C 5/3425; B07C 5/365; G01N 21/718
(Continued)

(56) References Cited

U.S. PATENT DOCUMENTS 5,143,224 A * 9/1992 Burchell ............... B07C 5/3425
                                                  209/579
6,753,957 B1   6/2004 Graft et al.
(Continued)

FOREIGN PATENT DOCUMENTS

DE          4426475 A1    2/1995
DE      102012015812 A1   2/2013
(Continued)

OTHER PUBLICATIONS

International Search Report from International Application No. PCT/US2015/036617, dated Sep. 24, 2015 (4 pages).
(Continued)

*Primary Examiner* — Terrell H Matthews
(74) *Attorney, Agent, or Firm* — Kagan Binder, PLLC

(57) ABSTRACT

A LIBS measurement system is described herein that provides an orifice, aperture or opening in a substantially V-shaped chute or sleeve that allows access to the material to be analyzed from the underside of the chute. The laser beam is aimed through the hole and return light (signal) is collected through the hole by a photodetector assembly. A diverter device, which is located at an output end of the chute, diverts certain particles away from the chute upon receipt of an actuation signal.

20 Claims, 4 Drawing Sheets

(51) Int. Cl.
  *B07C 5/342* (2006.01)
  *B07C 5/36* (2006.01)
  *G01J 3/443* (2006.01)

(52) U.S. Cl.
  CPC ............... *B07C 2501/0018* (2013.01); *B07C 2501/0036* (2013.01); *G01J 3/443* (2013.01)

(58) Field of Classification Search
  USPC ........................................ 209/577, 576, 579
  See application file for complete search history.

(56) References Cited

U.S. PATENT DOCUMENTS

| | | | | |
|---|---|---|---|---|
| 6,795,179 | B2* | 9/2004 | Kumar | B07C 5/3425 |
| | | | | 209/579 |
| 7,763,820 | B1* | 7/2010 | Sommer, Jr. | B07C 5/342 |
| | | | | 209/576 |
| 7,821,634 | B2 | 10/2010 | Dillon et al. | |
| 8,902,422 | B2* | 12/2014 | Chesner | G01J 3/443 |
| | | | | 356/318 |
| 2003/0132142 | A1 | 7/2003 | Kumar | |
| 2013/0079918 | A1 | 3/2013 | Spencer et al. | |
| 2013/0100444 | A1* | 4/2013 | Chesner | G01J 3/443 |
| | | | | 356/318 |
| 2018/0147607 | A1* | 5/2018 | Comtois | B07C 5/342 |

FOREIGN PATENT DOCUMENTS

| | | |
|---|---|---|
| EP | 1300200 A1 | 4/2003 |
| EP | 2832458 A1 | 2/2015 |
| GB | 1520858 A | 8/1978 |
| WO | 2012/040769 A1 | 4/2012 |
| WO | WO-2012040769 A1 * | 4/2012 ............ G01J 3/0208 |
| WO | 2013/145873 A1 | 10/2013 |

OTHER PUBLICATIONS

Written Opinion from International Application No. PCT/US2015/036617, dated Sep. 24, 2015 (7 pages).

* cited by examiner

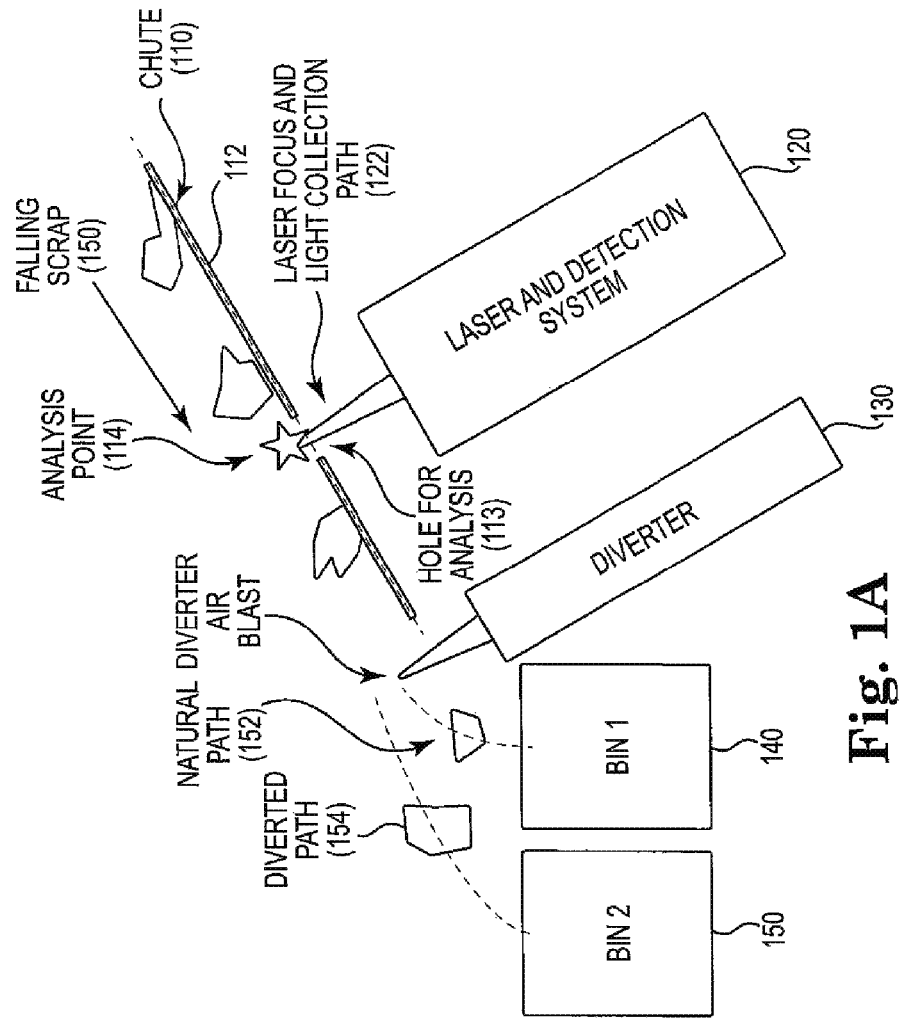
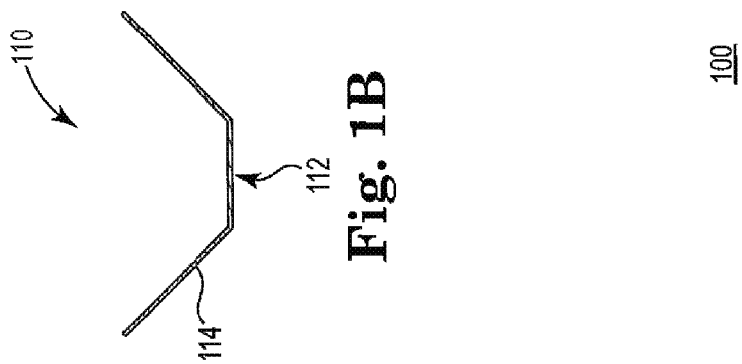

RAPID MATERIAL ANALYSIS USING LIBS SPECTROSCOPY

PRIORITY CLAIM TO PROVISIONAL APPLICATION

This application claims priority to U.S. Provisional Patent Application No. 62/015,756, filed Jun. 23, 2014, the entire contents of which are incorporated herein by reference in its entirety.

FIELD AND BACKGROUND

The invention is generally in the field of laser-induced breakdown spectroscopy (LIBS) and more particularly to a method and a system for conducting LIBS analysis of material moving on a conveyor system.

For various applications, methods are needed for determining the material constitution of a sample. A known method is laser-induced breakdown spectroscopy (LIBS), which involves focusing a laser beam onto a surface of the sample with a high enough power density to transform a small part of the sample material into a state of plasma. Optical emissions from the plasma plume are collected with light collection optics, and the spectral distribution (i.e. intensity as a function of wavelength) of the collected optical emissions is analyzed in a wavelength-sensitive detector such as a spectrometer that produces information in electronic form describing the spectral distribution. Since atomic and molecular constituents of sample materials have characteristic optical emission spectra, the information produced by the spectrometer reveals the constituents of that part of the sample onto which the laser beam was focused or directed.

The sample may in principle be solid, liquid or gaseous. In the case of a gaseous sample the concept of a "surface" of the sample does not exist, but the laser beam is just focused into the gaseous sample. Drawbacks of known LIBS measurement devices include their bulky structure and limited applicability to field use. In certain applications, LIBS measurement systems are able to characterize various samples in terms of elemental concentrations. In other applications, the type of material, such as a particular alloy composition can be identified with or without the determination of exact elemental concentrations. A primary advantage of the LIBS technology over XRF (x-ray fluorescence) is its ability to determine the elemental concentration of light elements such as Li, B, Be, C, Al, Na and Mg.

In U.S. Pat. No. 6,795,179 to Kumar, there is disclosed a metal particle sorting system that includes a conveyor for conveying randomly shaped scrap metal pieces in a random orientation, an image detector for electronically recording the image of a predefined viewing area through which the scrap pieces are conveyed by a traditional flat conveyor system, a position detector for detecting movement of the conveyor belt, a laser system configured to provide a laser beam including a stream of a plurality of laser pulses within a selected time interval, and at least one laser scanner assembly including a positionable beam deflector to direct the laser pulses at a selected piece at any location in a selected target region on the conveyor and a focusing element mounted downstream of the source of the laser pulses from the beam deflector to focus the beam and provide uniform laser power density along a plane. The system further includes a light collector for collecting light from plasma produced on the pieces as they are irradiated by the laser pulses, a light distribution and spectral analyzer system for isolating and measuring at least one selected band from the collected light, a separator to divert pieces to different bins based on discriminator signals, and control logic for continuously acquiring an image of the selected viewing area of the conveyor, processing the image to identify and locate the scrap pieces as they pass through the viewing area, monitoring the laser system to determine when the next laser pulses will be available, selecting a downstream location on the conveyor at which the next available stream of pulses of radiation may be directed at an identified piece, operating the scanner assemblies as required to direct the pulses to the selected target location, analyzing spectral data collected from the plasma, generating a discriminator signal based at least in part upon the spectral data analysis, and selectably activating the separator as a function of the discriminator signal to sort the analyzed pieces. Although apparently effective, this system is equipment- and investment-intensive as several scanner assemblies for generating plasma samples are required as well as control logic for continuously acquiring and processing images of the selected viewing area of the conveyor among other components.

In U.S. Pat. No. 6,753,957 to Graft et al., a system and a method is disclosed for mineral sorting and detecting, including remote sensing, and more particularly, for real-time detection and content evaluation of minerals or trace concentrations of elements in materials as they are conveyed on a moving belt. The Graft et al. invention employs a laser-induced breakdown spectroscopy (LIBS) system wherein intensity ratios of the emission lines characteristic of specific elements or minerals enable detection of the same while on a moving belt. Because associated minerals have different chemical compositions, namely, major or minor elements, the relative intensities, defined by their characteristic spectral lines, enable all phases to be consistently identified and assessed within a short time that is consistent with both LIBS and the moving belt system.

SUMMARY

There is provided herein a method and system for using a LIBS system for conducting rapid material analysis on material traveling along a conveyor or chute, thereby providing spectral measurements quickly and with a reasonably high degree of accuracy for the intended industrial and commercial application.

In one example embodiment, metal sorting is performed without the need to do laser scanning as in other prior art systems. Instead, each piece of material to be sampled is isolated in a vibrating chute carrying the material thereby avoiding the need for scanning the laser. The laser beam is shot or projected through the bottom of the chute (through a slot or hole) to which the surface of the metal or sample material piece is constrained by gravity, alleviating the need to move the LIBS laser focus in the vertical dimension. By its shape the chute is designed to further constrain the pieces in the side-to-side direction, forcing each piece to move over the hole in the chute. The data that is captured is analyzed by using specific spectral lines to distinguish between material types. The materials are then sorted by an air nozzle or a diverter system according to its composition.

In various example embodiments of the invention there is provided a method of laser spectroscopy on particles or pieces of material moving along a fixed or stationary material chute that is economical, accurate and faster than prior art systems. Such embodiments contrast with traditional implementations which fire laser light at pieces or particles from above the conveyor belt. In one example embodiment, a LIBS measurement system provided herein includes providing a hole or opening in a substantially V-shaped chute that allows access to the material to be analyzed from the underside of the chute. The laser beam is aimed through the hole and return light (signal) is collected through the hole by a photodetector. The advantages of the aforementioned examples over the traditional sampling method include, but are not limited to: 1) every piece is aligned with the hole in the chute via the V-shape (or concave-shaped) of the chute. Hence every piece can be sampled and little to no segregation occurs. 2) The position of each piece relative to the laser and optical focus is fixed by the chute and force of gravity. Each piece, if sliding on the chute and therefore touching the chute, has a known position. No autofocus and only a moderate depth of field are required. 3) Since the x, y, and z positions of the hole and surface of the piece are known, no motion technology is required, improving reliability and thus the industrial viability of the system. The type of laser and its method of operation are new to the commercial LIBS sorting market.

The common implementation of measurement from above a conveyor belt has significant problems: 1) If the laser spectroscopy system is fixed in space, items on the belt are not completely sampled. The laser system is only sampling at one point, e.g. the centerline. Vibration and motion on the belt typically make items segregate by size, and so at any fixed point only a sub-sample of particle/piece sizes are sampled. 2) Sampling from above requires either an autofocus or a large depth of field for the optical system. The former introduces complexity and may reduce sampling speed; the latter introduces additional uncertainty over a more focused optical system. 3) Implementations from above a belt that have tried to track every piece (for example, the LIBS system from Fraunhofer ILT (Aachen, Germany) for sorting metal scrap) have used 3D cameras and moving mirrors to aim a laser system at moving pieces. This complexity is enormous and impacts industrial reliability and viability of the system.

The novel features of the various embodiments of the invention itself, both as to its construction and its method of operation, together with additional advantages thereof, will be best understood from the following description of specific embodiments when read in connection with the accompanying drawings.

BRIEF DESCRIPTION OF THE DRAWINGS

FIGS. 1A-1B illustrate schematically an example embodiment of a LIBS measurement system and a side view of a flow chute according to the teachings herein;

DETAILED DESCRIPTION OF THE INVENTION

Figure 2:
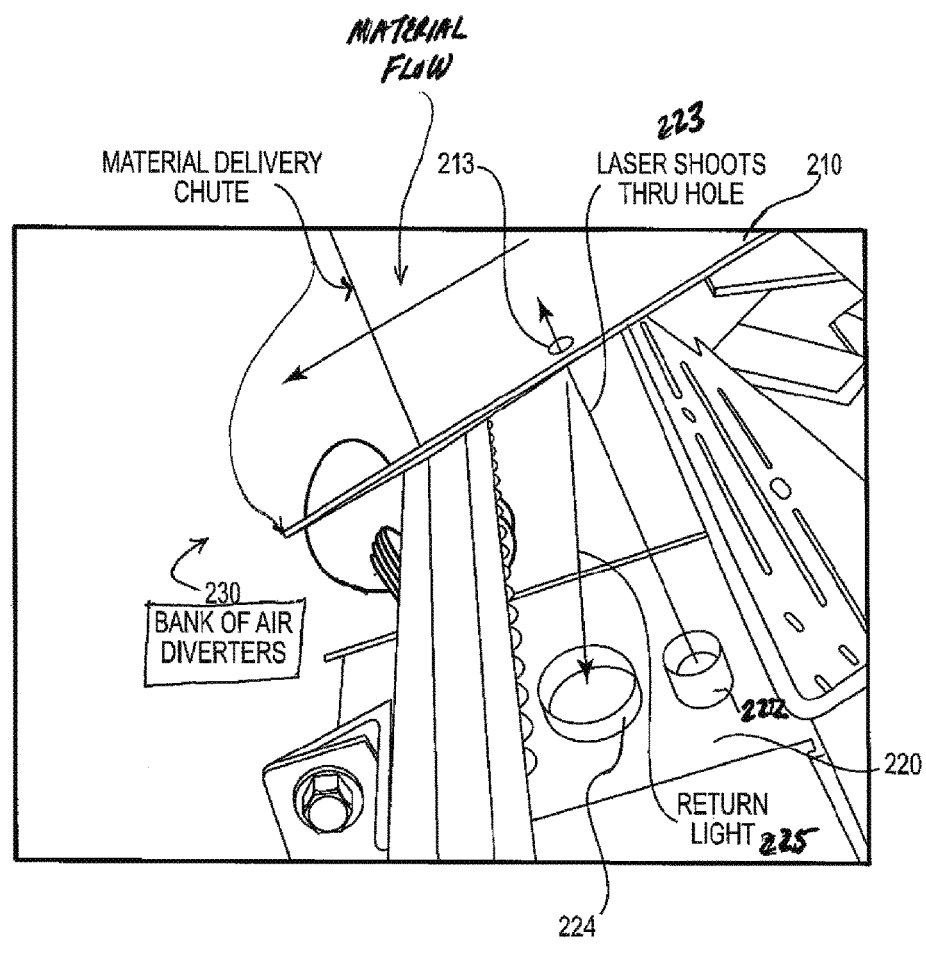
FIG. 2 illustrates an example embodiment of a LIBS measurement system according to the teachings herein.

Following are more detailed descriptions of various related concepts related to, and embodiments of, methods and apparatus according to the present disclosure. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

In one example embodiment of the invention, there is provided a bulk sampling and laser-targeting system to provide for material identification of a bulk stream of material including a flow chute having a feeder end and an output end, the output end adapted to extend at an angle away from the feeder end such that the flow chute is at an incline and the bulk stream of material flows along the flow chute gravitationally, the flow chute having a substantially concave-shaped configuration including an aperture disposed at a point of maximum concavity or trough of the flow chute that is a distance from the feeder end such that the bulk stream of material can form into an orderly flow down the chute. The system also includes a LIBS laser system disposed adjacent the aperture and configured to direct a pulsed laser beam through the aperture and into a material flowing through the flow chute, the aperture having a size sufficient to permit the laser beam to pass through to individual particles of the flowing material and to permit radiation from the individual particles to transmit back through the aperture. In addition, a radiation detection device is included that is disposed adjacent the aperture and adapted to collect the radiation emitted from the individual particles of material, wherein the radiation detection device is communicatively coupled to the LIBS laser system that includes a spectrometer and a controller, the spectrometer configured to identify a composition of the individual particles flowing in the chute. Finally, in a related embodiment the system includes at least one particle diverter device disposed adjacent the output end of the chute and adapted to divert the individual particle towards a collection system, wherein the at least one particle diverter device is communicatively coupled to the controller and is adapted to actuate upon receipt of a signal from the controller.

In another embodiment, there are provided a bulk sampling and laser-targeting system to provide for material identification of a bulk stream of material that includes a flow chute having a feeder end and an output end, the output end adapted to extend at an angle away from the feeder end such that the flow chute is at an incline and the bulk stream of material flows along the flow chute gravitationally, the flow chute having a substantially v-shaped configuration including an aperture disposed near the point of the maximum concavity of the V of the flow chute that is a distance from the feeder end such that the bulk stream of material can form into an orderly flow down the chute. Further, a LIBS laser system is included that is disposed adjacent the aperture and configured to direct a pulsed laser beam through the aperture and into a material flowing through the flow chute, the aperture having a size sufficient to permit the laser beam to pass through to individual particles of the flowing material and to permit radiation from the individual particles to transmit back through the aperture. The system further includes a radiation detection device that is disposed adjacent the aperture and adapted to collect the radiation emitted from the individual particles of material, wherein the radiation detection device is communicatively coupled to the LIBS laser system that includes a spectrometer and a controller, the spectrometer configured to identify a composition of the individual particles flowing in the chute from radiation received through a pierced mirror assembly configured to allow the laser beam to pass from a back side of the mirror assembly and through a hole of the mirror, while a front side of the mirror assembly is configured to substantially reflect the return light out of the laser beam path and onto a radiation detector optics of the radiation detection device. The system finally includes, in a related embodiment, at least one particle diverter device disposed adjacent the output end of the chute and adapted to divert the individual particle towards a collection system, wherein the at least one particle diverter device is communicatively coupled to the controller and is adapted to actuate upon receipt of a signal from the controller.

In yet another embodiment, a method is provided of bulk sampling and laser-targeting of a bulk stream of material that includes the steps of providing an angled flow chute having a feeder end and an output end adapted to extend at an angle away from the feeder end such that the flow chute is at an incline and the bulk stream of material flows along the flow chute gravitationally, the flow chute having a substantially v-shaped configuration including an aperture or orifice disposed in the center of the trough of the flow chute that is some distance from the feeder end such that the bulk stream of material can form into an orderly flow down the chute. In addition, the method includes the step of directing a laser beam, from a LIBS laser system disposed adjacent the aperture, through the aperture and ablating a material flowing through the flow chute, the aperture having a size sufficient to permit the laser beam to pass through to individual particles of the flowing material and to permit radiation from the ablated individual particles to transmit back through the aperture; collecting radiation emitting through the aperture from the individual ablated material particles and directing them to a spectrometer in the LIBS laser system having a controller therein, the spectrometer configured to identify a composition of the individual particles flowing in the chute. The method further includes, in a related embodiment, providing at least one particle diverter device disposed adjacent the output end of the chute and adapted to divert the individual particle towards a collection system, wherein the at least one particle diverter device is communicatively coupled to the controller and is adapted to actuate upon receipt of a signal from the controller.

Referring now to FIGS. 1A and 1B, FIG. 1A illustrates schematically a LIBS measurement system 100 for material sorting according to an embodiment of the invention. In this example embodiment, LIBS measurement 100 includes a concave sampling chute 110, a laser and detection system 120, a diverter 130 and material bins 140 and 150. In this example embodiment, chute 110, as can be seen in FIG. 1B, includes a planar floor 112 bounded by a set of side walls 114. In this example embodiment, a material to be analyzed travels down a concave or substantially V-shaped chute 110 on floor 112 as falling scrap 150 and moves past an analysis hole 113 on floor 112 of chute 110 through which a LIBS (laser induced breakdown system) laser system 120 projects a laser beam 122 through hole 113. Laser beam 122 then impinges unto and ablates individual particles of falling scrap 150 that are exposed through hole or orifice or aperture 113 (also known as an analysis point 114). An example of a LIBS laser and detection system is taught in U.S. Pat. No. 6,795,179 to Kumar, which is incorporated herein by reference in its entirety.

Diverter device 130, in this example embodiment, is communicatively coupled (wired or wirelessly (for example, RF or Bluetooth)) to laser and detection system 120 such that it is actuated to direct or divert certain scrap samples 152 and 154 to either bin 140 or bin 150. In this example embodiment, scrap sample 152 falls naturally into bin 140 by the force of gravity without the need for diverter 130 and sample 154 is diverted by diverter 130 into bin 150. In a related embodiment, depending on the location of the bins and the number of bins, diverter 130 is actuated to divert samples into various bins depending on the instructions received from laser and detection system 120. In this example embodiment, diverter 130 is an air nozzle, an air pump or blower configured to emit shots of air to divert samples 152 or 154. In a related embodiment, diverter 130 includes a member that pushes a sample in the direction of one of the collection bins or collection system, (such as paddles, levers, etc.), or that blocks the forward motion of a sample.

In related embodiments, chute 110 is formed into other configurations, such as a V-shaped channel or a U-shaped channel that allows material to move down the concave-shaped flow chute. In other embodiments, the flow chute is one of the following configurations: a U-shape with perpendicular sides; U-shaped with flat bottom side; a U-shape with sides angled outward and flat bottom; and a U-shape with sides angled outward and a curved bottom. In yet another embodiment, the flow chute is a ramp with a vibration mechanism operatively coupled thereto to promote downward flow of the stream of material. In another embodiment, the chute includes a vibration mechanism operatively coupled thereto to promote downward flow of the stream of material. In yet another embodiment, the flow chute (or sleeve) includes a pipe or cylinder structure with an orifice at the midpoint and bottom surface of the pipe, from which a laser beam can project up and through the orifice.

In various embodiments, the incline or angle of chute 110 is within, but is not limited to, a range of between about 20 degrees to about 70 degrees. At low angles, such as between about 20 to about 30 degrees, a vibrating chute or ramp can also be used. In other embodiments, material speed/chute angle correlations can be determined so as to then correlate to the speed of material moving by the analysis hole on the chute with the laser pulses through the aperture. The speed of the material will also be material-dependent with the laser measurement being virtually instantaneous.

Normally, there are irregularities in the shape of the material targets, but if these are within range of the laser focus, this eliminates the need for autofocus. In a related embodiment, autofocus is used in system 100 when the irregularly shaped targets are out of range of laser focus. One of the advantages of LIBS measurement system 100 is that the user does not need to track the sample pieces on a wide moving belt, as in prior art implementations.

In one example embodiment, the laser repetition rate of laser detector system 120 is about 20 Hz, but the laser repetition rate can be matched to the speed of the sample piece presentation at a hole 113. The LIBS laser energy must be sufficient to cause a spark at the sample and provide an analysis sufficient to characterize the sample. In this example embodiment, a 200 mJ laser with a long focal length was used and resulted in a depth of focus through the hole that was big enough to accommodate variations of more than 1 inch in the focus of the laser on the sampled material (which could result from piece irregularities in shape). In this example embodiment, a laser light 122 passes through beam shaping optics (not shown) before being focused on the pieces 150 with a focusing lens. In the simplest configuration, a single focusing lens could be used.

In this example embodiment, the photodetectors (not shown) used to detect light in the plasma or plume from the sampled material are amplified Si (silicon) photodiodes with a UV enhancement of the type similar to Thorlabs APD120A2. However, any photodetector could be used to capture the emission signal. In this example embodiment, an elemental line filter with about a 5 nm bandpass was used to isolate the emission lines emitted by the sample material. In related embodiments, other ways of collecting the light and isolating the emission include the combination of an elemental line filter with a photomultiplier tube detector, or the combination of a spectrometer to disperse the light and a detector to detect one or more particular wavelengths. In one example embodiment, a detector/line filter pair was used for each element, but in other implementations a single spectrometer was used to measure many elements simultaneously. Examples of rapid spectral analysis of the optical emissions are taught in U.S. Pat. No. 6,753,957, which is incorporated herein by reference in its entirety. Generally, the photodetection system is hermetically-sealed and may include input/output windows that are purged as needed.

FIG. 2 illustrates an example embodiment of a material sorting system using a LIBS measurement system 200 according to an embodiment of the invention. In this example embodiment, LIBS measurement 200 includes a sampling chute 210, a laser and detection system 220, at least one photodetector 224, a bank of diverters 230 and at least one material bin 240 (not shown). In this example embodiment, chute 210 is substantially V-shaped as the sampled material moves down the chute by gravity since the channel is pitched at an angle towards the ground. In this example embodiment, a material to be analyzed travels down chute 210 and moves past an analysis hole 213 (disposed preferably at the maximum point of concavity) of chute 210 through which laser system 220 projects a laser beam 222. As the laser beam passes through a hole 213 (see 223) it impinges unto the falling scrap that is exposed through hole 213 (also known as an analysis point 214) (not shown) and generates a spectral emission 225 in the form of return light. In a related embodiment, hole 213 is covered with a transparent/translucent member to help keep dust off the main lens of the laser. A cleaning or blower assembly can also be included to clean all lenses in the laser system. An example of a LIBS laser and detection system is aught in U.S. Pat. No. 6,795,179 to Kumar, which is incorporated herein by reference in its entirety.

In this example embodiment, the laser of LIBS system 200 fires at the samples from below and through hole or aperture 213, which may vary in size, but in this example the hole is about between 0.25 and 0.375 inches in diameter. One of the benefits is that gravity pulls the falling scrap pieces down the chute and keeps them on chute 210. This allows the sample to be a known distance (the floor of the chute) from the laser, and the substantially "V" shape of the chute concentrates most of the material samples in the center of the chute aligned with hole 213. The bottom portion 212 of the chute 210 can be narrower or wider, based on the piece size, or the chute can be continuously curved with no flat bottom. A bank of diverters 230, in this example embodiment, is communicatively coupled to laser and detection system 220 such that it is actuated to direct or divert certain scrap samples to at least one collection bin or collection system. In this example embodiment, diverters 230 are configured to blow magnesium (Mg) pieces out of a stream of predominantly aluminum (Al) pieces. In this example embodiment, diverters 230 include air pumps or air nozzles or a blower configured to emit shots of air to divert material samples to a certain bin. In a related embodiment, diverters 230 include members that push samples in the direction of a bin or another chute, such as a physical diverter consisting of a wall, a movable paddle or lever, and a controllable trap door at the floor of the flow chute.

Figure 3:
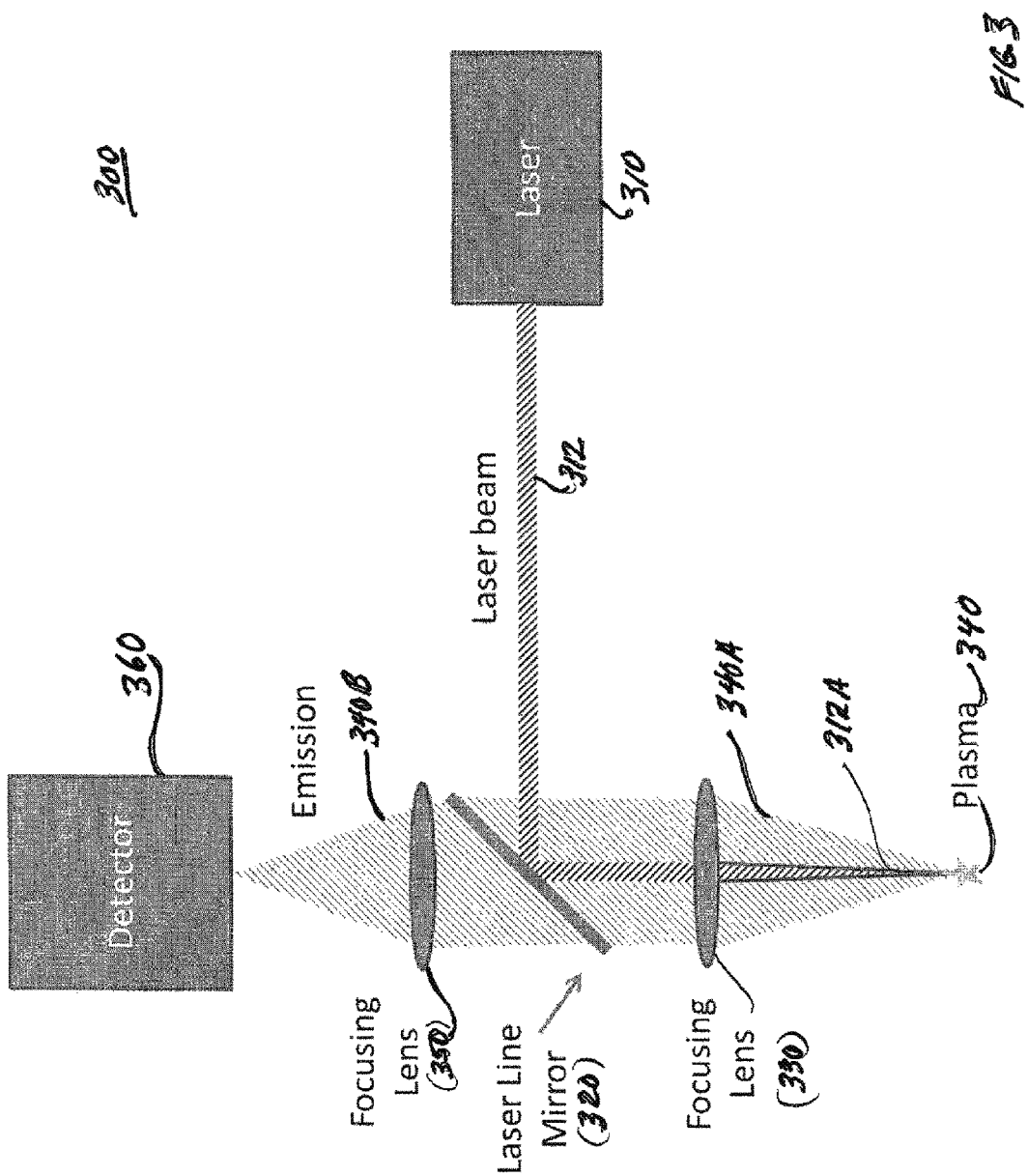
FIG. 3 illustrates an example embodiment of the laser and detection system of systems 100 and 200 for the collection of light from a plasma formed on a surface of an analyzed material.

Referring now to FIG. 3, there is illustrated an example embodiment of an optics configuration of a laser and detection system 300 according to the invention. Specifically, laser 310 emits a laser beam 312 which impinges on a laser line mirror 320 and reflects laser beam 312 towards a focusing lens 330. Lens 330 concentrates laser beam 312 into a focused beam 312A that ablates a material sample so as to emit a plasma 340. Light 340A from plasma 340 is collimated as it travels back through lens 330 and then passes through another focusing lens 350, converting it into a focused beam 340B that is collected by a detector 360. In this advantageous example, the return light from the sample passes through the same lens that focused the laser, and thereby is efficiently collected and collimated, rather than being collected through a separate lens. This configuration can be used in either laser and detection system of systems 100 or system 200 for the collection of light from a plasma formed on a surface of an analyzed material.

Figure 4:
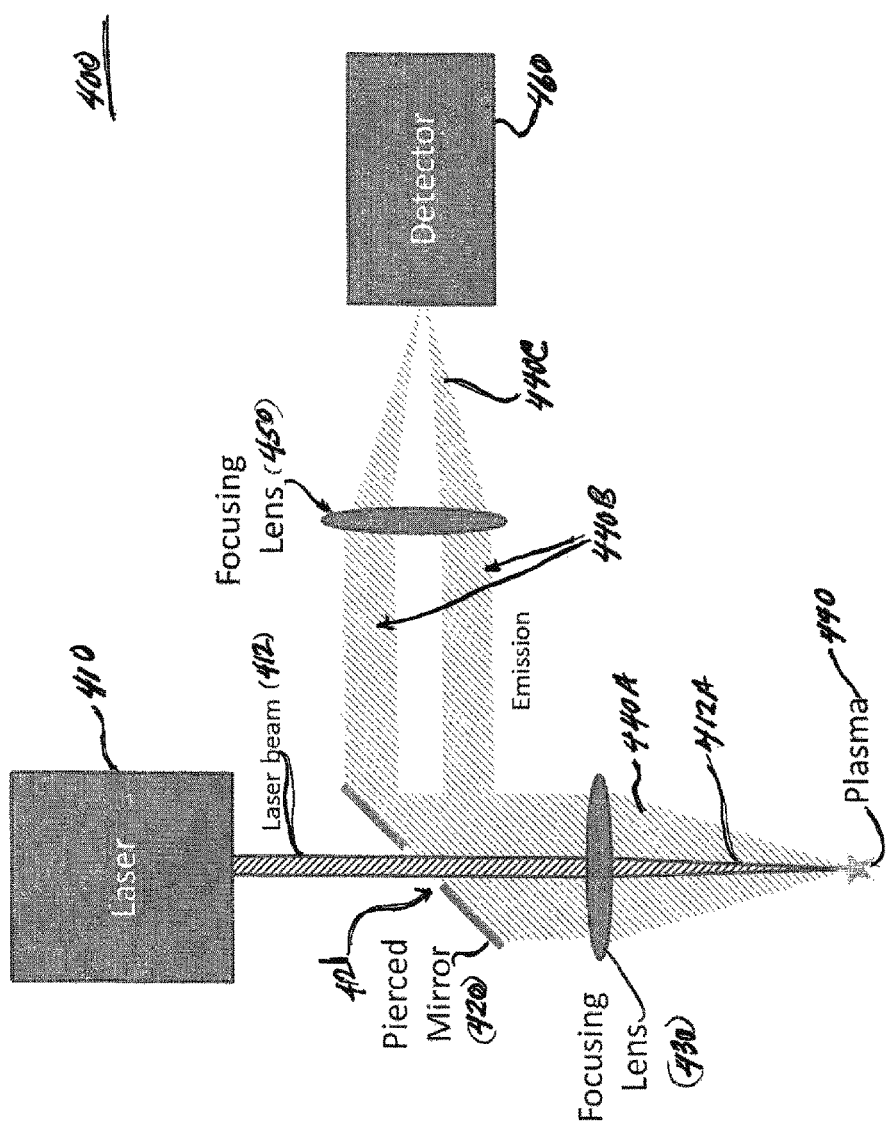
FIG. 4 illustrates another example embodiment of a pierced mirror assembly that can be used in either systems 100 and 200 according to the teachings herein.

Referring now to FIG. 4, there is illustrated another example embodiment of a pierced mirror assembly 420 forming part of an optics configuration 400 for a laser and detection system according to the invention. Specifically, laser 410 emits a laser beam 412 which passes through a hole 421 in pierced mirror assembly 420 and impinges on a focusing lens 430. Lens 430 concentrates laser beam 412 into a focused beam 412A that ablates a material sample and forms plasma 440. Light 440A from plasma 440 is collimated as it travels back through lens 430 and impinges on pierced mirror assembly 420. The collimated light from 440A is then reflected by pierced mirror assembly (except for the portion in the center of the collimated light from 440A corresponding to the hole in the pierced mirror 420) to form beam 440B, and then travels through another focusing lens 450 to form focused beam 440C that is collected by a detector 460. In this advantageous example optics configuration, the pierced mirror assembly inside the device is used to allow the laser to pass through a hole (coming from the back side) of the mirror, while the front side of the mirror reflects the return light out of the laser beam path and onto the detector optics. This arrangement can be used in either laser and detection system 100 or system 200.

In various embodiments described herein, laser parameters include, but are not limited to, active/passive Q-switched configurations; diode and/or lamp pumped configurations; OPO and/or Non-OPO configurations; and Nd:YAG, Er:glass or other viable semiconductor material can be used. The laser system can operate at any laser wavelength, for example for Nd:YAG in wavelengths of 1064 nm, 532 nm, 355 nm, 266 nm, or 213 nm, and with energy of laser pulses in the J (Joule), mJ (millijoule), microJ (microjoule) range, hence any laser energy sufficient to cause a plasma to form at the focal point of the optics. Similarly, any pulse duration of laser (e.g. nanosecond, picosecond, or femtosecond) and repetition rate (aperiodic to kHz rates or more) may be used, if sufficient to cause a plasma to form on the material to be analyzed.

Primary applications for the LIBS systems taught herein include but are not limited to: aluminum scrap sorters and secondary aluminum smelters which accept aluminum scrap, to value and verify the scrap as it comes in. Other applications include analysis of other non-ferrous metals, ferrous metals, refractory materials, and soils.

The following patents that relate to such LIBS devices are herein incorporated by reference in their entirety and constitute part of the disclosure herein: U.S. Pat. Nos. 6,753, 957; 6,795,179; 7,763,820; and 7,821,634 and U.S. Patent Publication No. 2013/0079918.

Having thus described several illustrative embodiments, it is to be appreciated that various alterations, modifications, and improvements will readily occur to those skilled in the art. Such alterations, modifications, and improvements are intended to be part of this disclosure, and are intended to be within the spirit and scope of this disclosure. While some examples presented herein involve specific combinations of functions or structural elements, it should be understood that those functions and elements may be combined in other ways according to the present invention to accomplish the same or different objectives. In particular, acts, elements, and features discussed in connection with one embodiment are not intended to be excluded from similar or other roles in other embodiments. Accordingly, the foregoing description and attached drawings are by way of example only, and are not intended to be limiting.

We claim:

1. A bulk sampling and laser-targeting system to provide for material identification of a bulk stream of material comprising:
a flow chute having a feeder end and an output end, the output end adapted to extend at an angle away from the feeder end such that the flow chute is at an incline and the bulk stream of material flows along the flow chute gravitationally, the flow chute having a substantially concave-shaped, open configuration along a length of the flow chute, the flow chute including an aperture disposed at a point of maximum concavity of the flow chute that is distal to the feeder end;
a LIBS laser system disposed adjacent the aperture and configured to direct a pulsed laser beam through the aperture, the aperture having a defined x, y, z location with respect to the laser beam, and into a material flowing through the flow chute, the aperture having a size sufficient to permit the laser beam to pass through to individual particles of the flowing material and to permit radiation from the individual particles to transmit back through the aperture; and
a radiation detection device disposed adjacent the aperture and adapted to collect the radiation emitted from the individual particles of material, wherein the radiation detection device is communicatively coupled to the LIBS laser system that includes a spectrometer and a controller, the spectrometer configured to identify a composition of the individual particles flowing in the chute.

2. The system of claim 1 further comprising:
at least one particle diverter device disposed adjacent the output end of the chute and adapted to divert the individual particle towards a collection system, wherein the at least one particle diverter device is communicatively coupled to the controller and is adapted to actuate upon receipt of a signal from the controller.

3. The system of claim 2 wherein the at least one particle diverter includes a diverter device adapted to emit a burst of pressurized air when actuated at one or more individual particles of material so as to divert the individual particle towards the collection system.

4. The system of claim 1 wherein the radiation detection device includes a pierced mirror assembly configured to allow the laser beam to pass from a back side of the mirror assembly and through a hole of the mirror, while a front side of the mirror assembly is configured to substantially reflect the return light out of the laser beam path and onto a radiation detector optics.

5. The system of claim 2 wherein the collection system comprises a first collection bin for receiving the diverted particles.

6. The system of claim 5 wherein the collection system comprises a second collection bin for receiving particles traveling on a natural path from the output end of the chute.

7. The system of claim 1 further comprising a cleaning assembly configured to maintain optics of the LIBS and the radiation detection system substantially dust-free.

8. The system of claim 1 further comprising a transparent or translucent member disposed over the aperture.

9. The system of claim 1 wherein a repetition rate of the LIBS laser beam is a function of the speed of material flow along the flow chute and wherein the speed of material flow along the flow chute is a function of the angle of the chute.

10. The system of claim 2 wherein the at least one diverter device includes a physical diverter selected from the group consisting of a wall, a movable paddle or lever, and a controllable trap door at the floor of the flow chute.

11. The system of claim 1, wherein the concave-shaped flow chute has a substantially V-shaped configuration.

12. The system of claim 1, wherein the concave-shape of the flow chute is selected from the group consisting of a U-shape with perpendicular sides; U-shaped with flat bottom side; a U-shape with sides angled outward and flat bottom; and a U-shape with sides angled outward and a curved bottom.

13. The system of claim 12, further comprising a vibration mechanism operatively coupled to the flow chute to promote downward flow of the stream of material.

14. The system of claim 1, wherein the flow chute comprises a ramp with a vibration mechanism operatively coupled thereto to promote downward flow of the stream of material.

15. A bulk sampling and laser-targeting system to provide for material identification of a bulk stream of material comprising:
a flow chute having a feeder end and an output end, the output end adapted to extend at an angle away from the feeder end such that the flow chute is at an incline and the bulk stream of material flows along the flow chute gravitationally, the flow chute having a substantially v-shaped, open configuration along a length of the flow chute, the flow chute including an aperture disposed at a point of maximum concavity of the flow chute that is distal to the feeder end;
a LIBS laser system disposed adjacent the aperture and configured to direct a pulsed laser beam through the aperture, the aperture having a defined x, y, z location with respect to the laser beam, and into a material flowing through the flow chute, the aperture having a size sufficient to permit the laser beam to pass through to individual particles of the flowing material and to permit radiation from the individual particles to transmit back through the aperture; and
a radiation detection device disposed adjacent the aperture and adapted to collect the radiation emitted from the individual particles of material, wherein the radiation detection device is communicatively coupled to the LIBS laser system that includes a spectrometer and a controller, the spectrometer configured to identify a composition of the individual particles flowing in the chute from radiation received through a pierced mirror assembly configured to allow the laser beam to pass from a back side of the mirror assembly and through a hole of the mirror, while a front side of the mirror assembly is configured to substantially reflect the return light out of the laser beam path and onto a radiation detector optics of the radiation detection device.

16. The system of claim 15 further comprising at least one particle diverter device disposed adjacent the output end of the chute and adapted to divert the individual particle towards a collection system, wherein the at least one particle diverter device is communicatively coupled to the controller and is adapted to actuate upon receipt of a signal from the controller.

17. The system of claim 16 wherein the at least one particle diverter includes a diverter device adapted to emit a burst of pressurized air when actuated at one or more individual particles of material so as to divert the individual particle towards the collection system.

18. The system of claim 16 wherein the at least one diverter device includes a physical diverter selected from the group consisting of a wall, a movable paddle or lever, and a controllable trap door at the floor of the flow chute.

19. A method of bulk sampling and laser-targeting of a bulk stream of material comprising the steps of:

providing an angled flow chute having a feeder end and an output end adapted to extend at an angle away from the feeder end such that the flow chute is at an incline and the bulk stream of material flows along the flow chute gravitationally, the flow chute having a substantially v-shaped, open configuration along a length of the flow chute, the flow chute including an aperture or orifice disposed at a nadir or trough of the flow chute that is distal to the feeder end;

directing a laser beam, from a LIBS laser system disposed adjacent the aperture, through the aperture and ablating a material flowing through the flow chute, the aperture having a defined x, y, z location with respect to the laser beam and having a size sufficient to permit the laser beam to pass through to individual particles of the flowing material and to permit radiation from the ablated individual particles to transmit back through the aperture;

collecting radiation emitting through the aperture from the individual ablated material particles and directing the radiation to a spectrometer in the LIB S laser system having a controller therein, the spectrometer configured to identify a composition of the individual particles flowing in the chute; and providing at least one particle diverter device disposed adjacent the output end of the chute and adapted to divert the individual particle towards a collection system, wherein the at least one particle diverter device is communicatively coupled and responsive to the controller and is adapted to actuate upon receipt of a signal from the controller.

20. The method of claim 19 in which said step of collecting radiation emission from said flow chute includes providing a pierced mirror assembly configured to allow the laser beam to pass from a back side of the mirror assembly and through a hole of the mirror, while a front side of the mirror assembly is configured to substantially reflect the return light out of the laser beam path and onto radiation detector optics.

* * * * *

UNITED STATES PATENT AND TRADEMARK OFFICE
CERTIFICATE OF CORRECTION

PATENT NO. : 10,088,425 B2  
APPLICATION NO. : 15/321143  
DATED : October 2, 2018  
INVENTOR(S) : Steven G. Buckley et al.

Page 1 of 1

It is certified that error appears in the above-identified patent and that said Letters Patent is hereby corrected as shown below:

On the Title Page

(72) should read: Steven G. Buckley, Redmond, WA (US)
   Darrick L. Niccum, Vadnais Heights, MN (US)
   – Ricky Roland Comtois, Austin, TX (US) –

Signed and Sealed this
Ninth Day of July, 2019

Andrei Iancu
*Director of the United States Patent and Trademark Office*